United States Patent [19]

Voegell et al.

[11] Patent Number: 4,901,712

[45] Date of Patent: Feb. 20, 1990

[54] BONE NAILER

[75] Inventors: Douglas W. Voegell; Robert L. Assell, both of St. Paul, Minn.

[73] Assignee: Minnesota Mining and Manufacturing Company, St. Paul, Minn.

[21] Appl. No.: 185,058

[22] Filed: Apr. 22, 1988

[51] Int. Cl.⁴ .......................... A61F 5/04; B25C 7/00
[52] U.S. Cl. ...................................... 606/75; 227/147
[58] Field of Search ....... 128/92 YD, 92 YC, 92 VD, 128/92 VT, 92 YF; 227/147

[56] References Cited

U.S. PATENT DOCUMENTS

| | | | |
|---|---|---|---|
| 516,074 | 3/1894 | Brock | 227/147 |
| 541,038 | 6/1895 | Clark | 227/147 |
| 776,393 | 11/1904 | Harriman et al. | 227/147 |
| 924,054 | 6/1909 | Gehne | 227/147 |
| 2,229,868 | 1/1941 | Newell, Sr. | 227/147 |
| 2,588,738 | 3/1952 | Lundgren | 227/147 |
| 2,643,379 | 6/1953 | Natovich | 227/147 |
| 2,927,324 | 3/1960 | Ollig et al. | 1/46 |
| 3,036,482 | 5/1962 | Kenworthy et al. | 227/147 |
| 3,060,440 | 10/1962 | Pfaff et al. | 227/147 |
| 3,641,590 | 2/1972 | Michele | 3/1 |
| 4,109,735 | 8/1978 | Bent | 173/163 |
| 4,298,074 | 11/1981 | Mattchen | 173/129 |
| 4,367,836 | 1/1983 | Hodson | 227/147 |
| 4,403,725 | 9/1983 | Lawrence | 227/147 |
| 4,414,967 | 11/1983 | Shapiro | 128/92 E |
| 4,462,395 | 7/1984 | Johnson | 128/92 X C |
| 4,500,025 | 2/1985 | Skwor | 227/19 |
| 4,527,726 | 7/1985 | Assell et al. | 227/19 |
| 4,540,110 | 9/1985 | Bent deceased et al. | 227/8 |
| 4,562,948 | 1/1986 | Floyd | 227/147 |
| 4,569,469 | 2/1986 | Mongeon et al. | 227/19 |
| 4,648,541 | 3/1987 | Mongeon | 227/19 |
| 4,676,424 | 6/1987 | Meador et al. | 227/147 |

Primary Examiner—Robert A. Hafer
Assistant Examiner—Michael Brown
Attorney, Agent, or Firm—Donald M. Sell; Walter N. Kirn; Stephen W. Bauer

[57] ABSTRACT

A bone nailer adapted for use with an elongate nail or screw like insert that has a head portion, and a smaller diameter embedable portion projecting from the head portion. The nailer includes a housing having an inner surface defining a through passageway with a portion of the inner surface adjacent an outlet opening of the passageway being adapted to receive the insert with its head portion farthest from the outlet opening and to guide the head portion during movement of the insert through the outlet opening. A driver having an end adapted to engage the head portion is mounted on the housing for sliding movement from a load position with the driver spaced from the outlet opening to afford positioning the insert in the passageway, along the passageway so that the end of the driver can push the insert toward the outlet opening, to an eject position at which the driver has pushed the insert out the outlet opening so that drive assembly adapted to be manually activated can rapidly propel the driver along the passageway from its load to its eject position to rapidly move the insert through the outlet opening and embed its embedable portion in adjacent bone.

15 Claims, 2 Drawing Sheets

BONE NAILER

TECHNICAL FIELD

The present invention relates to surgical devices adapted to drive inserts into bone to hold portions of bone together and/or attach items to bone, and in one particular aspect, to such devices adapted to drive nail or screw like inserts into bone.

BACKGROUND ART

U.S. Pat. No. 4,414,967 describes rapidly and reproducibly imparting a controlled amount of energy from a stapler to a staple to drive the staple into bone, and U.S. Pat. Nos. 4,500,025; 4,540,110; 4,527,726; 4,569,469; and 4,648,541 describe various bone stapler embodiments adapted to drive staples into bone in the manner described in U.S. Pat. No. 4,414,967. While such stapling of bone has proved quite successful for many types of procedures, there are procedures in which it is desirable to drive a screw or nail like insert into bone, for example to attach items such as ligaments to bones. Heretofore such inserts could only be applied manually through the use of manually manipulated hammers or screwdrivers which is a slow process, and presents problems of unwanted transverse relative movement as the inserts are engaged with the bone.

DISCLOSURE OF INVENTION

The present invention provides a bone nailer adapted to rapidly and reproducibly impart a controlled amount of energy to nail or screw like inserts to quickly embed them in bone with a minimum of unwanted transverse relative movement.

According to the present invention there is provided a bone nailer adapted for use with an elongate nail or screw like insert comprising a head portion, and an embedable portion projecting from the head portion and having a smaller transverse cross sectional area than the head portion. The nailer comprises a housing having an inner surface defining a through passageway extending from an inlet opening to an outlet opening, with a portion of the inner surface adjacent the outlet opening being adapted to receive the insert with its head portion farthest from the outlet opening and its embedable portion projecting from the head portion toward the outlet opening, and to guide the head portion during movement of the insert through the outlet opening. A driver having an end adapted to engage the head portion is mounted on the housing for sliding movement from a load position with the driver spaced from the outlet opening to afford positioning the insert in the passageway, along the passageway so that the end of the driver can push the insert toward the outlet opening, to an eject position at which the driver has pushed the insert out the outlet opening. Also, drive means adapted to be manually activated are provided for rapidly propelling the driver along the passageway from its load to its eject position to rapidly move the insert through the outlet opening and embed its embedable portion in adjacent bone.

Preferably, that portion of the inner surface defining the passageway that is adapted to receive the insert includes a holding part spaced from the outlet opening adapted for an interference fit with the head of the insert with an end of the insert opposite the head slightly projecting through the outlet opening, and a guiding part between the holding part and the outlet opening adapted for a close clearance fit with the head portion of the insert to accurately guide the head portion during movement of the insert through the outlet opening.

Also, preferably the bone nailer comprises a cartridge assembly adapted for releasable engagement with a drive assembly that provides the handle assembly 14 for the Bone Stapler 10 described in U.S. Pat. No. 4,648,541 (the content whereof is incorporated herein by reference), which drive or handle assembly comprises a drive assembly housing 24, a piston assembly 40 mounted in the housing 24 for rapid movement in a first direction between first and second positions, and means for manually operating the drive assembly to afford rapid movement of the piston assembly 40 between its first and second positions. The cartridge assembly for use with that handle assembly 14 can comprise the elongate nail or screw like insert, a cartridge housing defining the through passageway in which the insert is positioned, and the driver; with the cartridge housing being adapted to be removably mounted on the drive assembly housing with the axis of the passageway aligned in the first direction and the driver positioned so that movement of the piston assembly between its first and second positions rapidly propels the driver along the passageway from its load to its eject position to rapidly move the insert through the outlet opening and embed its embedable portion in adjacent portions of bone.

Such a cartridge housing can be made of a polymeric material with the cartridge assembly being intended for only a single use. Alternatively, the cartridge housing can be made of metal and intended for repeated use, in which case the cartridge assembly may further include an elongate punch adapted to help load inserts into the cartridge housing.

BRIEF DESCRIPTION OF DRAWING

The present invention will be further described with reference to the accompanying drawing wherein like reference numerals refer to like parts in the several views, and wherein.

DETAILED DESCRIPTION

Figure 1:
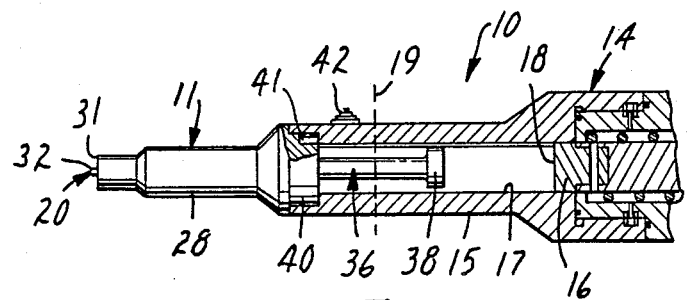
FIG. 1 is a fragmentary side view of a bone nailer according to the present invention with parts in section to show detail.

Referring now to the drawing, there is shown a bone nailer according to the present invention generally designated by the reference numeral 10.

Generally the bone nailer 10 comprises a cartridge assembly 11 adapted for use with a drive assembly 14.

The drive assembly 14 preferably is the handle assembly 14 illustrated and described in U.S. Pat. No.

4,648,541 (the content whereof is incorporated herein by reference) without the barrel assembly 12 described in that patent. Generally, as illustrated in FIG. 1, that drive assembly 14 comprises a drive assembly housing 15, a piston assembly 16 mounted in a cylindrical chamber 17 in the housing 15 for rapid movement in a first direction along the axis of the chamber 17 between a first position illustrated in FIG. 1, and a second position at which an end 18 of the piston assembly 16 will be about at the dotted line 19, and means for manually operating the drive assembly 14 (such as the trigger operated compressed air system described in U.S. Pat. No. 4,648,541) to afford rapid movement of the piston assembly 16 between its the first and second positions.

The cartridge assembly 11 comprises an elongate nail like insert or nail 20 comprising a head portion 21 having inner and outer end surfaces 22 and 23 and a peripheral surface 24 extending between the end surfaces 22 and 23, and a coaxial embedable portion 25 projecting from the inner end surface 22 of the head portion 21 and having a significantly smaller transverse cross section area than the head portion 21. Also included in the cartridge assembly 11 is a cartridge housing 28 having a cylindrical inner surface 29 defining a through passageway having an axis and extending from an inlet opening 30 to an outlet opening 31. A portion of the cylindrical inner surface 29 adjacent the outlet opening 31 of about the length of the nail 20 receives the nail 20 with the head portion 21 farthest from the outlet opening 31 and the embedable portion 25 projecting from the head portion 21 toward the outlet opening 31 and is adapted to guide the peripheral surface 24 of the head portion 21 during movement of the nail 20 through the outlet opening 31. That portion of the cylindrical inner surface 29 includes a holding part 33 that has a slight interference fit with the peripheral surface 24 of the nail 20 and is spaced from the outlet opening 31 so that a pointed distal end 32 of the embedable portion 25 of the insert 20 opposite the head portion 21 projects slightly through the outlet opening 31 where it can be pressed against and thereby located along the surface of bone into which it is to be embedded (alternatively the pointed end 32 of the insert 20 could be flush with or recessed from the outlet opening 31 in which case the cartridge housing 28 could optionally have pointed locating projections flanking the outlet opening 31). That portion of the cylindrical inner surface 29 also includes a guiding part 35 between the holding part 33 and the outlet opening 31 adapted for a close clearance fit with the peripheral surface 24 of the nail 20 (the increase in diameter of the guiding part 35 with respect to the holding part 33 being exaggerated in the drawing to afford visual distinction between the parts 33 and 35) so that the guiding part 35 will accurately guide the head portion 21 of the nail 20 as the nail 20 is propelled from within the cartridge housing 28 into adjacent bone.

The cartridge assembly 11 further includes a driver 36 having an end 37 adapted to engage the outer surface 23 of the head portion 21 on the nail 20, and a headed end 38 adapted to be engaged by the piston assembly 16. Prior to use of the cartridge assembly 11, a portion of the driver 36 adjacent its end 37 is mounted in the cartridge housing 28 in a load position with its end 37 spaced from the outlet opening 31 (at which load position the driver 36 is retained by a rubber O ring 39 around a groove in the driver 36 and frictionally engaged with the inner surface 29) and the insert 20 is positioned in the passageway. The driver 36 is movable along the passageway with the end 37 pushing the insert 20 to an eject position (not shown) at which the end 37 of the driver 36 pushes the insert 20 out the outlet opening 31.

The cartridge housing 28 is adapted to be removably mounted on the drive assembly housing 15 as illustrated in FIG. 1 with the axis of the passageway defined by the inner surface 29 coaxial with the axis of the chamber 17 and the driver 36 positioned so that movement of the piston assembly 16 between its first and second positions rapidly propels the driver 36 along the passageway from its load to its eject position to rapidly move the insert 20 through the outlet opening 31 and embed its embedable portion 25 in adjacent bone. Such removable engagement of the cartridge housing 28 with the drive assembly housing 15 is afforded by structure included in the drive assembly 14 described in U.S. Pat. No. 4,648,541 from column 5 line 63 through column 6 line 41 adapted to receive a cylindrical outer surface 40 on the cartridge housing 28, engage L-shaped recesses 41 from the outer surface, and be releasably retained in engagement by means operated by a button 42 to release the cartridge assembly 11.

Figure 4:
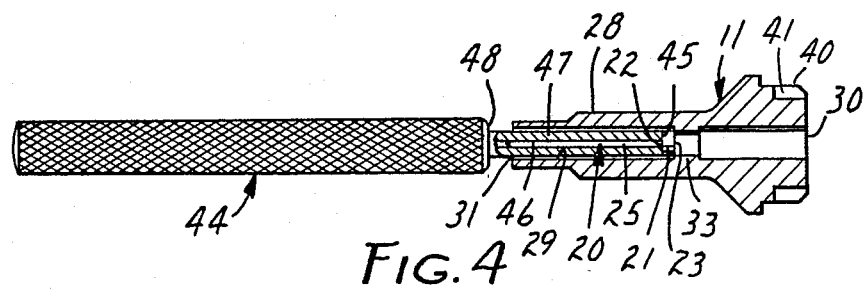
FIG. 4 is a reduced side view partially in section, of a cartridge housing including in the cartridge assembly of FIGS. 1, 2 and 3 being reloaded through the use of a punch.

The cartridge housing 28 may, as illustrated, be made of metal (e.g., stainless steel) and intended for repeated uses, or may be made of a polymeric material (e.g., polycarbonate) and be intended for a single use in which case the driver 36 may also be of the same material and be temporarily staked to the housing 28 (e.g., by an adhesive or sonic welding) rather than having the o ring 39 to hold it place before firing. When the cartridge housing 28 is intended for repeated uses, the cartridge assembly 11 may further include an elongate punch 44 as is illustrated in FIG. 4, which punch 44 is adapted to position the insert or nail 20 at a predetermined position in the passageway with the head 21 of the nail 20 in the holding part 33 of the inner surface 29. The punch 44 has a first end surface 45, a coaxial socket 46 opening through the first end surface 45 adapted to receive the embedable portion 25 of the nail 20 with the inner surface 22 of its head 21 against the first end surface 45 of the punch 44, an end portion 47 adjacent its first end surface 45 adapted to freely enter the passageway in the cartridge housing 28 through the outlet opening 31, and a shoulder 48 too large to enter the passageway at the end of the end portion 47 opposite the first end surface 45, the distance between the first end surface 45 and the shoulder 48 being selected to position the head 21 of the nail 20 at the predetermined distance within the passageway when the embedable portion 25 of the nail 20 is positioned in the socket 46 and the end portion 47 of the punch 44 is inserted and pressed into the passageway to the depth permitted by the shoulder 48. Subsequent to inserting the nail 20 in the passageway through the use of the punch 44, the driver 36 can also be manually inserted into the passageway through its inlet opening 30 to complete loading of the cartridge assembly 11.

Figures 5, 6:
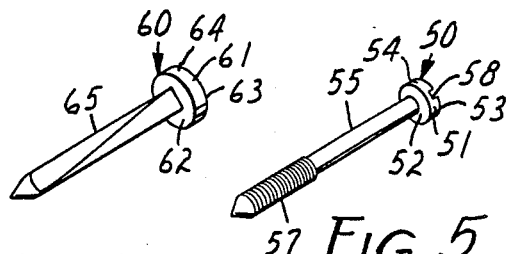
FIGS. 5 and 6 show alternate embodiments of inserts that can be included in the cartridge assemblies of FIGS. 1 through 3.
Figure 2:
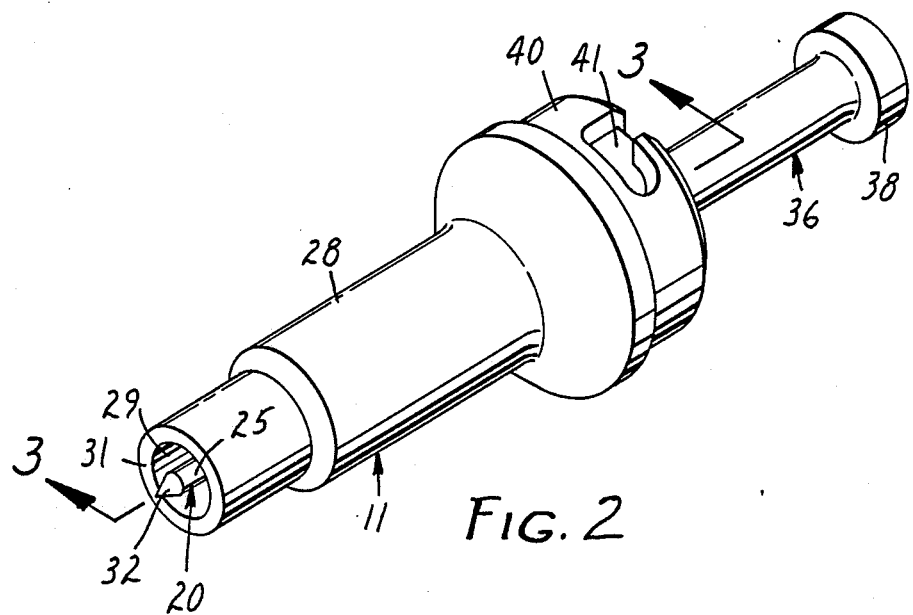
FIG. 2 is an enlarged perspective view of a cartridge assembly included in the bone nailer of FIG. 1.
Figure 3:
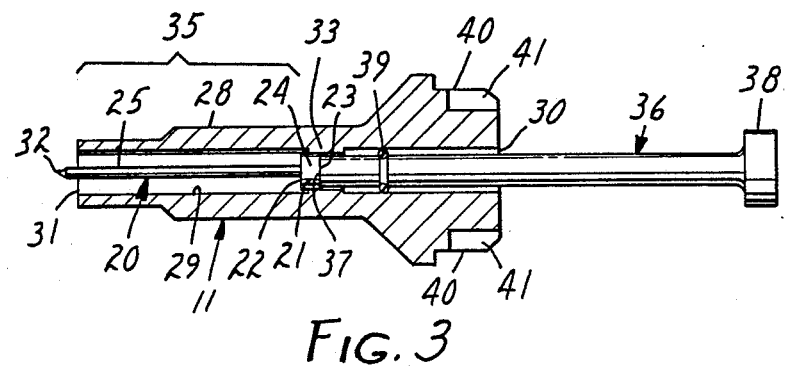
FIG. 3 is a reduced sectional view taken approximately along line 3—3 of FIG. 2.

FIGS. 5 and 6 illustrate alternate embodiments of nail or screw like inserts 50 and 60 that may be included in the cartridge assembly FIGS. 1 through 4 instead of the nail 20.

The elongate screw like insert or screw 50 illustrated in FIG. 5 comprises a head portion 51 having inner and outer end surfaces 52 and 53 and a peripheral surface 54 extending between the end surfaces 52 and 53, and a coaxial embedable portion 55 projecting from the inner end surface 52 of the head portion 51, having a significantly smaller transverse cross sectional area than the head portion 51, and having threads 57 along a distal end part of the embedable portion 55. After being driven into bone, the screw 50 can be removed by rotating it through the use of a screwdriver engaged with a transverse slot 58 in the head portion 51.

The elongate nail like insert or nail 60 illustrated in FIG. 6 comprises a head portion 61 having inner and outer end surfaces 62 and 63 and a peripheral surface 64 extending between the end surfaces 62 and 63, and a coaxial embedable portion 65 with a generally rectangular cross section projecting from the inner end surface 62 of the head portion 61, having a significantly smaller transverse cross sectional area than the head portion 61, and having a helical twist along its length. Upon being driven, the nail 60 will rotate upon engagement with bone to make firm engagement therewith.

Figure 7:
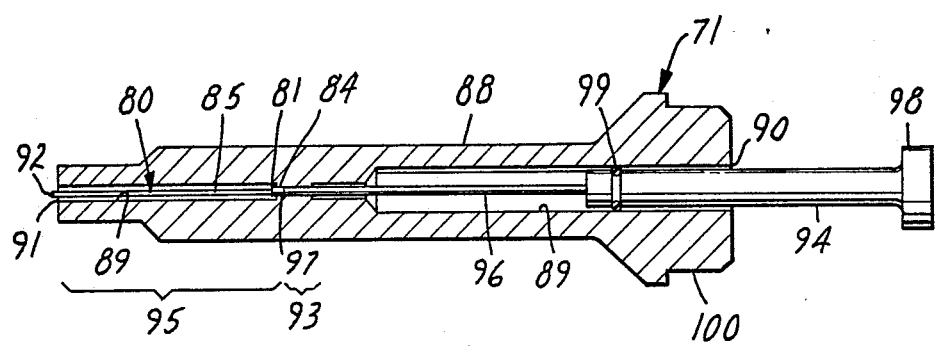
FIG. 7 is a longitudinal sectional view of an alternative embodiment of a cartridge assembly according to the present invention.

Referring now to FIG. 7, there is illustrated an alternative embodiment of a cartridge assembly 71 according to the present invention that comprises an elongate nail like insert or nail 80 comprising a head portion 81 having inner and outer end surfaces and a peripheral surface 84 extending between the end surfaces, and a coaxial embedable portion 85 of almost the same diameter as the head portion 81 projecting from the inner end surface of the head portion 81 and having a slightly smaller transverse cross sectional area than the head portion 81. The cartridge assembly 71 is particularly adapted for use when it is desired to have the head portion 81 of the nail 80 embedded in bone into which it is driven. Also included in the cartridge assembly 71 is a cartridge housing 88 having a cylindrical inner surface 89 defining a through passageway having an axis and extending from an inlet opening 90 to an outlet opening 91. A portion of the cylindrical inner surface 89 adjacent the outlet opening 91 of about the length of the nail 80 receives the nail 80 with the head portion 81 farthest from the outlet opening 91 and the embedable portion 85 projecting from the head portion 81 toward the outlet opening 91 and is adapted to guide the peripheral surface 84 of the head portion 81 during movement of the nail 80 through the outlet opening 91. That portion of the cylindrical inner surface 89 includes a holding part 93 that has a slight interference fit with the peripheral surface 84 of the nail 80 and is spaced from the outlet opening 91 so that a pointed distal end 92 of the embedable portion 85 of the insert 80 opposite the head portion 81 projects slightly through the outlet opening 91 where it can be pressed against and thereby located along the surface of bone into which it is to be embedded (alternatively the pointed end 92 of the insert 80 could be flush with or recessed from the outlet opening 91 in which case the cartridge housing 88 could optionally have pointed locating projections flanking the outlet opening 91). That portion of the cylindrical inner surface 89 also includes a guiding part 95 between the holding part 93 and the outlet opening 91 adapted for a close clearance fit with the peripheral surface (the increase in diameter of the guiding part 95 with respect to the holding part 93 being exaggerated in the drawing to afford a visual distinction between the parts 93 and 95) of the nail 80 so that the guiding part 95 will accurately guide the head portion 81 of the nail 80 as the nail 80 is propelled from within the cartridge housing 88 into adjacent bone.

The cartridge assembly 71 further includes a stepped cylindrical driver 96 having an end 97 adapted to engage the outer surface of the head portion 81 on the nail 80, and a headed end 98 adapted to be engaged by the piston assembly 16. Prior to use of the cartridge assembly 71, a portion of the driver 96 adjacent its end 97 is mounted in the cartridge housing 88 in a load position with its end 97 spaced from the outlet opening 91 (at which load position the driver 96 is retained by a rubber O ring 99 around a groove in the driver 94 and frictionally engaged with the inner surface 89) and the insert 80 is positioned in the passageway. The driver 96 is movable along the passageway with the end 97 pushing the insert 80 to an eject position (not shown) at which the end 97 of the driver 96 pushes the insert 80 out the outlet opening 91.

The cartridge housing 88 is adapted to be removably mounted on the drive assembly 15 in the same manner as the cartridge housing 28 with the axis of the passageway defined by the inner surface 89 coaxial with the axis of the chamber 17 and the driver 96 positioned so that movement of the piston assembly 16 between its first and second positions rapidly propels the driver 96 along the passageway from its load to its eject position to rapidly move the nail 80 through the outlet opening 91 and embed its embedable portion 85 in adjacent bone. Such removable engagement of the cartridge housing 88 with the drive assembly 14 is afforded by the same structure on the drive assembly housing 15 indicated above that is adapted to receive a cylindrical outer surface 100 on the cartridge housing 88, engage L-shaped recesses (not shown) from the outer surface 100, and be releasably retained in engagement by means operated by the button 42 to release the cartridge assembly 71.

Like the cartridge housing 15, the cartridge housing 88 may be made of a polymeric material and be intended for a single use, or may be made of metal and intended for repeated uses.

The present invention has now been described with reference to two embodiments thereof. It will be apparent to those skilled in the art that many changes can be made in the embodiments described without departing from the scope of the present invention. For example, the inner surfaces 29 and 89 defining the passageways could optionally be formed with rifling adapted to engage the peripheral surfaces 24 and 84 of the head portions 21 and 81 to cause rotation of the inserts 20 or 80 as they are driven through the outlet openings 31 and 91. Also, the cartridge housing can be made long and slender to facilitate its use in arthroscopic surgery. Thus the scope of the present invention should not be limited to the structures described in this application, but only by structures described by the language of the claims and the equivalents of those structures.

We claim:

1. A bone nailer adapted for use with an elongate nail or screw like insert of the type comprising a head portion having inner and outer end surfaces and a peripheral surface extending between the end surfaces, and an embedable portion projecting from the inner end surface of the head portion and having a smaller transverse cross sectional area than the head portion, said nailer comprising:

a cartridge housing having an inner surface defining a through passageway extending from an inlet opening to an outlet opening, a portion of said inner surface adjacent said outlet opening being adapted to receive the insert with its head portion farthest from said outlet opening and its embedable portion projecting from the head portion toward the outlet opening, the portion of the inner surface defining the passageway including a holding part spaced from the outlet opening adapted for an interference fit with the peripheral surface of the head with an end of the embedable portion opposite the head slightly projecting through the outlet opening, and a guiding part between the holding part and the outlet opening adapted for close clearance fit with the peripheral surface of the head to guide the peripheral surface of the head portion during movement of the insert through the outlet opening;

a driver having an end adapted to engage the outer surface of the head portion and being mounted in said cartridge housing for sliding movement between a load position with the driver spaced from the outlet opening to afford positioning the insert in the passageway, along said passageway so that said end can push the insert toward the outlet opening, to an eject position at which the driver has pushed the insert out said outlet opening;

drive means adapted to be manually activated for rapidly propelling said driver along said passageway from said load to said eject position to rapidly move the insert through said outlet opening and embed its embedable portion in adjacent bone; and an elongate punch adapted to position an insert at a predetermined position in said passageway, said punch having a first end surface, a socket opening through said first end surface adapted to receive the embedable portion of the insert with the inner surface to the head against the first end surface of the punch, an end portion adjacent said first end surface adapted to freely enter said passageway, and a shoulder too larger to enter said passageway at the end of said end portion opposite said first end surface, the distance between said first end surface and said shoulder being selected to position the head of the insert a predetermined distance within said passageway when the embedable portion of the insert is positioned in said socket and said end portion of the punch is inserted into said passageway to the depth permitted by said shoulder.

2. A bone nailing system comprising:

an elongate nail or screw like insert comprising a head portion having inner and outer end surfaces and a peripheral surface extending between said end surfaces, and an embedable portion projecting from the inner end surface of said head portion and having a smaller transverse cross sectional area than said head portion;

a cartridge housing having an inner surface defining a through passageway extending from an inlet opening to an outlet opening, a portion of said inner surface adjacent said outlet opening receiving said insert with said head portion farthest from said outlet opening and said embedable portion projecting from said head portion toward said outlet opening, the portion of the inner surface defining the passageway including a holding part spaced from the outlet opening adapted for an interference fit with the peripheral surface of the head with an end of the embedable portion opposite the head slightly projecting through the outlet opening, and a guiding part between the holding part and the outlet opening adapted for a close clearance fit with the peripheral surface of the head to guide the peripheral surface of said head portion during movement of the insert through said outlet opening;

a driver having an end adapted to engage said outer surface of said head portion and being mounted in said cartridge housing in a load position with said driver spaced from the outlet opening and said insert in the passageway, said driver being movable along said passageway with said end pushing the insert to an eject position at which the driver pushes the insert out said outlet opening;

drive means adapted to be manually activated for rapidly propelling said driver along said passageway from said load position to said eject position to rapidly move said insert through said outlet opening and embed said embedable portion in adjacent bone; and an elongate punch adapted to position an insert at a predetermined position in said passageway, said punch having a first end surface, a socket opening through said first end surface adapted to receive the embedable portion of the insert with the inner surface of the head against the first end surface of the punch, an end portion adjacent said first end surface adapted to freely enter said passageway, and a shoulder too large to enter said passageway at the end of said end portion opposite said first end surface, the distance between said first end surface and said shoulder being selected to position the head of the insert a predetermined distance within said passageway when the embedable portion of the insert is positioned in said socket and said end portion of the punch is inserted into said passageway to the depth permitted by said shoulder.

3. A bone nailing system according to claim 2 wherein said insert has threads along said embedable portion.

4. A bone nailing system according to claim 2 wherein said embedable portion of said insert has a generally rectangular transverse cross section and a helical twist along its length.

5. A cartridge adapted for use with a drive assembly of the type comprising a drive assembly housing, a piston assembly mounted in the drive assembly housing for rapid movement in a first direction between first and second positions, and means for manually operating the drive assembly to afford movement of the piston assembly between the first and second positions, said cartridge comprising:

an elongate nail or screw like insert comprising a head portion having inner and outer end surfaces and a peripheral surface extending between said end surfaces, and an embedable portion projecting from the inner end surface of said head portion and having a smaller transverse cross sectional area than said head portion;

a cartridge housing having an inner surface defining a through passageway having an axis and extending from an inlet opening to an outlet opening, a portion of said inner surface adjacent said outlet opening receiving the insert with said head portion farthest from said outlet opening and said embedable portion projecting from said head portion toward said outlet opening, the portion of the inner surface defining the passageway including a holding part spaced from the outlet opening adapted for an interference fit with the peripheral surface of the head with an end of the embedable portion opposite the head slightly projecting through the outlet opening, and a guiding part between the holding part and the outlet opening adapted for a close clearance fit with the peripheral surface of the head to guide the peripheral surface of the head portion during movement of the insert through said outlet opening;

a driver having an end adapted to engage said outer surface of said head portion and being mounted in said cartridge housing in a load position with the driver spaced from said outlet opening and said insert in the passageway, said driver being movable along said passageway with said end pushing the insert to an eject position at which the driver pushes the insert out said outlet opening; and an elongate punch adapted to position an insert at a predetermined position in said passageway, said punch having a first end surface, a socket opening through said first end surface adapted to receive the embedable portion of the insert with the inner surface of the head against the first end surface of the punch, an end portion adjacent said first end surface adapted to freely enter said passageway, and a shoulder too large to enter said passageway at the end of said end portion opposite said first end surface, the distance between said first end surface and said shoulder being selected to position the head of the insert a predetermined distance within said passageway when the embedable portion of the insert is positioned in said socket and said end portion of the punch is inserted into said passageway to the depth permitted by said shoulder;

said cartridge housing having quick connect-disconnect means for removably mounting the cartridge housing on the drive assembly housing with the axis of said passageway aligned in said first direction and said driver positioned so that movement of the piston assembly between the first and second positions rapidly propels said driver along said passageway from said load to said eject position to rapidly move said insert through said outlet opening and embed said embedable portion in adjacent bone.

6. A cartridge according to claim 5 wherein said cartridge housing is of a polymeric material.

7. A cartridge according to claim 5 wherein said insert has threads along said embedable portion.

8. A cartridge according to claim 5 wherein said embedable portion of said insert has a generally rectangular transverse cross section and a helical twist along its length.

9. A cartridge according to claim 5 wherein the quick connect-disconnect means includes an engagement surface on the cartridge housing adapted to engage the drive assembly housing, with the engagement surface having a generally L-shaped recess therein for receiving a releasable retaining button extending from a portion of the drive assembly housing to removably mount the cartridge assembly on the drive assembly housing.

10. A cartridge according to claim 9 further comprising frictional-retaining means for mounting the driver on the cartridge housing in a portion of the passageway, with the end of the driver spaced from the outlet opening of the passageway, and for permitting the driver to move along the passageway from the load position to the eject position.

11. A cartridge according to claim 10 wherein the frictional-retaining means comprises walls along the driver defining an annular groove, and an elastomeric O-ring in the groove for frictionally engaging the inner surface of the cartridge housing to retain the driver in the passageway.

12. A cartridge assembly adapted for use with an elongate nail or screw like insert of the type comprising a head portion having inner and outer end surfaces and a peripheral surface extending between the end surfaces, and an embedable portion projecting from the inner end surface of the head portion and having a smaller transverse cross sectional area than the head portion; and adapted for use with a drive assembly of the type comprising a drive assembly housing, a piston assembly mounted in the drive assembly housing for rapid movement in a first direction between first and second positions, and means for manually operating the drive assembly to afford rapid movement of the piston assembly between the first and second positions, said cartridge assembly comprising:

a cartridge housing having an inner surface defining a through passageway having an axis and extending from an inlet opening to an outlet opening, a portion of said inner surface adjacent said outlet opening being adapted to receive the insert with the head portion of the insert farthest from said outlet opening and the embedable portion of the insert projecting from its head portion toward said outlet opening, the portion of the inner surface defining the passageway including a holding part spaced from the outlet opening adapted for an interference fit with the peripheral surface of the head with an end of the embedable portion opposite the head slightly projecting through the outlet opening, and a guiding part between the holding part and the outlet opening adapted for a close clearance fit with the peripheral surface of the head to guide the peripheral surface of the head portion during movement of the insert through the outlet opening;

a driver having an end adapted to engage the outer surface of the head portion of the insert and being mounted in said cartridge housing in a load position with the driver spaced from the outlet opening to afford positioning the insert in the passageway, said driver being movable along said passageway with said end pushing the insert to an eject position at which the driver pushes the insert out said outlet opening; and an elongate punch adapted to position an insert at a predetermined position in said passageway, said punch having a first end surface, a socket opening through said first end surface adapted to receive the embedable portion of the insert with the inner surface of the head against the first end surface of the punch, an end portion adjacent said first end surface adapted to freely enter said passageway, and a shoulder too large to enter said passageway at the end of said portion opposite said first end surface, the distance between said first end surface and said shoulder being selected to position the head of the insert a predetermined distance within said passageway when the embedable portion of the insert is positioned in said socket and said end portion of the punch is inserted into said passageway to the depth permitted by said shoulder;

said cartridge housing having quick connect-disconnect means for removably mounting the cartridge housing on the drive assembly housing with the axis of said passageway aligned in said first direction and said driver positioned so that movement of the piston assembly between the first and second positions rapidly propels said driver along said passageway from said load to said eject position to rapidly move the insert through said outlet opening and embed its embedable portion in adjacent bone.

13. A cartridge assembly according to claim 12 wherein the quick connect-disconnect means includes an engagement surface on the cartridge housing adapted to engage the drive assembly housing, with the engagement surface having a generally L-shaped recess therein for receiving a releasable retaining button extending from a portion of the drive assembly housing to removably mount the cartridge assembly on the drive assembly housing.

14. A cartridge assembly according to claim 13 further comprising frictional-retaining means for mounting the driver on the cartridge housing in a portion of the passageway, with the end of the driver spaced from the outlet opening of the passageway, and for permitting the driver to move along the passageway from the load position to the eject position.

15. A cartridge assembly according to claim 14 wherein the frictional-retaining means comprises walls along the driver defining an annular groove, and an elastomeric O-ring in the groove for frictionally engaging the inner surface of the cartridge housing to retain the driver in the passageway.

* * * * *

UNITED STATES PATENT AND TRADEMARK OFFICE
CERTIFICATE OF CORRECTION

PATENT NO. : 4,901,712

DATED : February 20, 1990

INVENTOR(S) : Douglas W. Voegeli and Robert L. Assell

It is certified that error appears in the above-identified patent and that said Letters Patent is hereby corrected as shown below:

On the title page item [19] should read --Voegell, et al--
Item [75] (Inventors:) "Voegell" should read --Voegeli--.

Col. 2, line 51, "including" should read --included--.

Col. 3, line 21, "section" should read --sectional--.

Col. 4, line 60, after "assembly" insert --of--.

Col. 7, line 7, after "for" insert --a--.

Col. 7, line 30, "to" should read --of--.

Col. 7, line 33, "larger" should read --large--.

Col. 10, line 55, after "said" (first occurrence) insert --end--.

Signed and Sealed this

Seventh Day of May, 1991

*Attest:*

HARRY F. MANBECK, JR.

*Attesting Officer*   *Commissioner of Patents and Trademarks*